United States Patent
Yamamoto

(10) Patent No.: US 7,053,378 B2
(45) Date of Patent: May 30, 2006

(54) RADIOGRAPHIC APPARATUS

(75) Inventor: Osamu Yamamoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 169 days.

(21) Appl. No.: 10/803,371

(22) Filed: Mar. 17, 2004

(65) Prior Publication Data

US 2004/0188626 A1    Sep. 30, 2004

(30) Foreign Application Priority Data

Mar. 25, 2003    (JP)    ............... 2003-083523

(51) Int. Cl.
   *G01T 1/24*    (2006.01)

(52) U.S. Cl. ............... 250/370.09; 250/370.11; 378/98.8; 378/62

(58) Field of Classification Search ......... 250/370.09, 250/370.08, 370.11, 580, 98.8; 378/98.8, 378/62

See application file for complete search history.

(56) References Cited

U.S. PATENT DOCUMENTS

| | | | | |
|---|---|---|---|---|
| 4,340,818 A | * | 7/1982 | Barnes | ............... 378/155 |
| 4,497,062 A | | 1/1985 | Mistretta et al. | |
| 5,526,442 A | * | 6/1996 | Baba et al. | ............... 382/132 |
| 5,661,309 A | * | 8/1997 | Jeromin et al. | ............... 250/580 |
| 5,804,832 A | * | 9/1998 | Crowell et al. | ............... 250/580 |
| 5,871,892 A | * | 2/1999 | Dickerson et al. | ............... 430/502 |
| 6,528,796 B1 | * | 3/2003 | Kaifu et al. | ............... 250/370.11 |
| 6,800,870 B1 | * | 10/2004 | Sayag | ............... 250/584 |
| 6,806,473 B1 | * | 10/2004 | Honda et al. | ............... 250/370.11 |
| 6,825,472 B1 | * | 11/2004 | Endo | ............... 250/370.09 |
| 6,855,936 B1 | * | 2/2005 | Yamamoto | ............... 250/370.09 |
| 6,888,144 B1 | * | 5/2005 | Rodricks | ............... 250/370.09 |
| 6,895,077 B1 | * | 5/2005 | Karellas et al. | ............... 378/98.3 |
| 2002/0090184 A1 | * | 7/2002 | Sayag | ............... 385/120 |

FOREIGN PATENT DOCUMENTS

| | | |
|---|---|---|
| GB | 2 270 825 | 3/1994 |
| JP | 2002-116281 | 4/2002 |

* cited by examiner

*Primary Examiner*—David Porta
*Assistant Examiner*—Faye Polyzos
(74) *Attorney, Agent, or Firm*—Morgan & Finnegan, L.L.P.

(57) ABSTRACT

A radiographic apparatus includes photoelectric converter elements for converting a radiographic image of an object into image signals and a shield member for shielding the photoelectric converter elements from scattered rays arising within the radiographic apparatus from radiation passing through the photoelectric converter elements. The shield member has a plurality of areas, in which at least one of a radiation transmittivity and a radiation scattering probability varies.

5 Claims, 7 Drawing Sheets

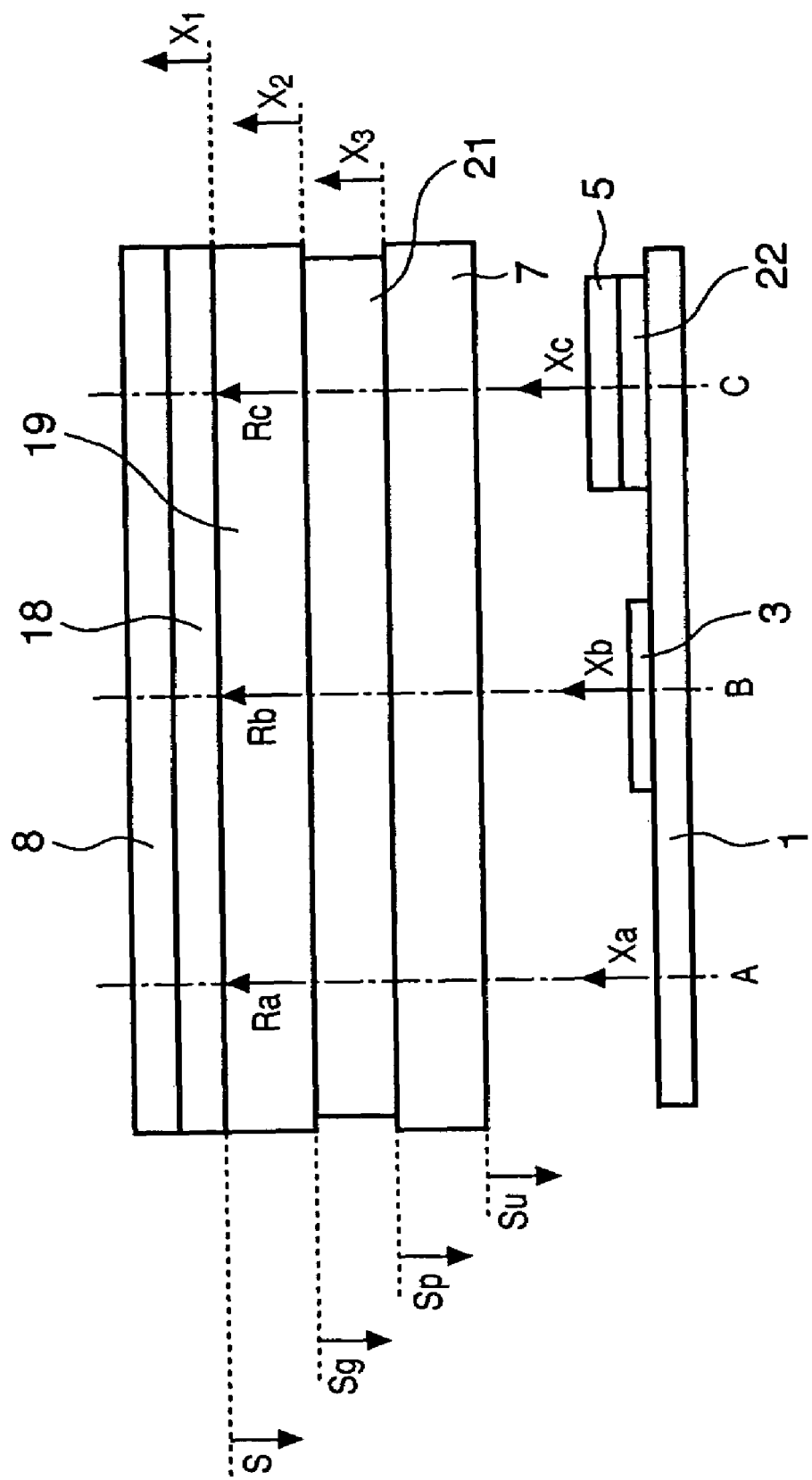

RADIOGRAPHIC APPARATUS

FIELD OF THE INVENTION

The present invention relates to a radiographic apparatus having an imager that includes a plurality of photoelectric converter elements.

BACKGROUND OF THE INVENTION

Conventionally, a method of irradiating an object with radiation and detecting the intensity distribution of the radiation that passes through the object in order to obtain a radiographic image of the object is widely used in industrial non-destructive testing, medical diagnoses and other fields. As a specific example of a typical method of obtaining a radiographic image of an object, there is one that employs a combination of so-called "phosphor sheets" (or intensifying paper), which emits fluorescent light when exposed to radiation, and silver-halide film, in which radiation passing through the object is converted into visible light by the phosphor sheet and the visible light forms a latent image on the silver-halide film, after which the silver-halide film is chemically processed in order to develop the latent image into a visible image. The radiographic image obtained by such a method is an analog image, used in diagnostics and testing.

By contrast, a technique for obtaining digital images using as the image receptor a two-dimensional array sensor comprised of picture elements, or pixels, arranged in a lattice or grid, with the pixels in turn comprised of tiny photoelectric converter elements, switching elements and the like, has recently been developed. A radiographic apparatus using this type of technology can display the acquired image data instantaneously, and is called a direct X-ray digital imaging apparatus. This type of digital radiographic apparatus has several advantages over the analog photograph technique, including the fact that it is filmless, that the images can be processed in ways that make the acquired information more useful, and that digital images easily lend themselves to the creation of databases FIG. 5 is a schematic diagram of a radiographic system that uses the two-dimensional array sensor described above.

As shown in the diagram, X-rays emitted from an X-ray source 12 of an X-ray generator irradiate an object (in this case a person P), with the X-rays passing through the object P reaching a two-dimensional array sensor 14 inside a radiographic apparatus housing 100 placed between the object P and a table 13. The two-dimensional array sensor 14 has a phosphor sheet that renders the X-ray image as visible light. The X-ray image rendered as visible light by the phosphor sheet is then converted into electrical signals by photoelectric converter elements that are sensitive to visible light and are arranged in a grid. The image information resulting from the conversion into electrical signals is then digitized by an AD (analog-digital) converter, not shown, and the digitized image information is processed by an image processor 15 into digital image data. An image based on this image data is then displayed on a monitor 16. Moreover, the digital image data can also be stored in a pre-existing digital storage device 17.

FIG. 6 is a diagram showing a schematic cross-sectional view of the internal arrangement of the X-ray imaging apparatus described above.

Inside the housing 100 of the X-ray imaging apparatus are disposed a phosphor sheet 8 that renders the X-rays as visible light, photoelectric converter elements 18 arranged in a grid for converting the visible light into electrical signals, a glass plate 19 that supports the photoelectric converter elements 18 from the back (as seen from the side from which the X-rays come), a base 7 that supports the glass plate 19 and an electrical circuit board 1 that receives the electrical signals from the photoelectric converter elements 18 through a flat cable 20 and performs AD conversion of the photo-electrically converted signals. In addition, an X-ray shield member 21 is disposed between the glass plate 19 and the base 7. Further, elements 3 and 22, comprising an amp for amplifying the electrical signals from the photoelectric converter elements 18, an IC for controlling the driving of the photoelectric converter elements 18, etc., as well as a protective layer 5, are disposed on the electrical circuit board 1.

In a radiographic apparatus like that described above, the X-rays pass through the glass plate 19 to reach the constituent elements of the lower layer without being completely absorbed by the phosphor sheet 8. The X-rays also pass through these elements as well, but some of the X-rays are reflected back to the phosphor sheet 8 as secondary X-rays (also called scattered rays). When these scattered rays are rendered as visible light by the phosphor sheet 8 they cause deterioration in contrast of the X-ray image of the object. The X-ray shield member 21 is provided in order to shield against these sorts of scattered rays, for which lead (Pb), with its low rate of X-ray transmittivity, is widely used.

The probability of scattering occurring and the probability of the X-rays passing through depend on the structure of the matter, as well as on the nature of the quality of the used X-rays.

FIG. 7 is a schematic diagram expressing the state of passage of the X-rays through each of the constituent elements of the apparatus. For simplicity, the quality of the X-rays is assumed to be monoenergetic.

If the amount of X-ray radiation transiting the material without being absorbed by the phosphor sheet 8 and the photoelectric converter elements 18 is S and the probability of scattering at the glass plate 19 is Gs, then the amount of scattered rays X1 per unit of surface area of the glass plate 19 can be expressed as $$X1 = S \cdot Gs \tag{1}$$

Similarly, if the probability of scattering at the X-ray shield member 21, the base 7, the electrical circuit board 1, the element 3 and the protective layer 5 is Ps, Us, As, Bs and Cs, respectively, then the amount of X-ray radiation scattering X2, X3, Xa, Xb and Xc at the X-ray shield member 21, the base 7, the electrical circuit board 1, the element 3 and the protective layer 5, respectively, is $$X2 = Sg \cdot Ps$$

$$X3 = Sp \cdot Us$$

$$Xa = Su \cdot As \tag{2}$$

$$Xb = Su \cdot Bs$$

$$Xc = Su \cdot Cs$$

Where Sg, Sp and Su are the amount of X-ray radiation passing through the glass plate 19, the X-ray shield member 21 and the base 7, respectively. Here, if the transmittivity at the glass plate 19 is Gt, then the amount of X-ray radiation Sg passing through the glass plate 19 is $$Sg = S \cdot Gt \tag{3}$$

Similarly, if the transmittivity of the X-ray shield member 21 and the base 7 is Pt and Ut, respectively, then the amount of X-ray radiation passing through the X-ray shield member 21 and the base 7, respectively Sp and Su, is $$Sp=Sg \cdot Pt$$

$$Sg=Sp \cdot Ut \qquad (4)$$

Therefore, substituting the equations in (3) and (4) for each of the equations in (2) yields $$X2=S \cdot Gt \cdot Ps$$

$$X3=S \cdot Gt \cdot Pt \cdot Us$$

$$Xa=S \cdot Gt \cdot Pt \cdot Ut \cdot As \qquad (5)$$

$$Xb=S \cdot Gt \cdot Pt \cdot Ut \cdot Bs$$

$$Xc=S \cdot Gt \cdot Pt \cdot Ut \cdot Cs$$

The amount of scattered rays returning as far as the phosphor sheet 8 is shown as the sum of the amount of scattered rays from each layer. If the amount of scattered rays per unit of surface area returning from a position A on the electrical circuit board 1 is Ra, then $$Ra=X1+Gt \cdot X2+Gt \cdot Pt \cdot X3+Gt \cdot Pt \cdot Ut \cdot Xa \qquad (6)$$

Therefore, $$Ra=S \cdot Gs+S \cdot Gt^2 \cdot Ps+S \cdot Gt^2 \cdot Pt^2 \cdot Us+S \cdot Gt^2 \cdot Pt^2 \cdot Ut^2 \cdot As \qquad (7)$$

Similarly, if the amount of scattered rays per unit of surface area returning to the phosphor sheet 8 from a position B of the element 3 and a position C of the protective layer 5 is Rb and Rc, respectively, then $$Rb=S \cdot Gs+S \cdot Gt^2 \cdot Ps+S \cdot Gt^2 \cdot Pt^2 \cdot Us+S \cdot Gt^2 \cdot Pt^2 \cdot Ut^2 \cdot Bs$$

$$Rc=S \cdot Gs+S \cdot Gt^2 \cdot Ps+S \cdot Gt^2 \cdot Pt^2 \cdot Us+S \cdot Gt^2 \cdot Pt^2 \cdot Ut^2 \cdot Cs \qquad (8)$$

In this manner, in order for scattered rays from constituent elements of the layer below the base 7 to return to the phosphor sheet 8, these scattered rays must pass through the base 7, the X-ray shield member 21 and the glass plate 19.

If the transmittivity Pt of the X-ray shield member 21 is low enough, then substantially all of the scattered rays are absorbed by the X-ray shield member 21 without reaching the phosphor sheet 8. As a result, the amount of scattered rays (that is, the amount of backscattering) from the lower layer can be held to insignificant levels at the X-ray image. Conversely, if the transmittivity of the X-ray shield member 21 is not low enough, then the differences in the amount of scattered rays from the electrical circuit board 1, the element 3 and the protective layer 5 (the effect of the last term in equations (7) and (8)) becomes exceptionally large and the differences between Ra, Rb and Rc appear as an image pattern in the X-ray image. Lead (Pb), with its X-ray low transmittivity, is commonly used as the material for the X-ray shield member 21. However, compared to other metals, lead lacks rigidity and is hard to handle, and for these reasons a member is required to support the lead, which complicates the structure of the apparatus. Moreover, the structure shown in FIG. 7 requires an X-ray shield member of approximately the same size as the two-dimensional array sensor, and therefore the use of high-density lead for the X-ray shield member 21 greatly increases the weight of the apparatus. In particular, with a portable (that is, hand-held) radiographic apparatus (also called an electronic cassette or a cassette-type radiographic apparatus) containing a two-dimensional array sensor, which is generally heavier than the conventional film cassette, the heavier the apparatus becomes the less portable it becomes and thus the harder it is to position correctly with respect to the object.

SUMMARY OF THE INVENTION

The present invention has been made in consideration of the above-described situation, and has as its object to provide a radiographic apparatus that reduces backscattering while holding down the weight of the radiographic apparatus.

According to the present invention, the foregoing object is attained by providing a radiographic apparatus comprising: an imaging unit for converting a radiation image of an object into an image signal; and a shield member for shielding the imaging unit from scattered rays arising inside the radiographic apparatus from radiation passing through the imaging unit, the shield member including a plurality of areas in which either a radiation transmittivity or a radiation scattering probability, or both, differs.

Other features and advantages of the present invention will be apparent from the following description when taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 7 is a schematic diagram expressing the state of passage of the X-rays through each of the constituent elements of the conventional apparatus.

DETAILED DESCRIPTION OF THE PREFERRED EMBODIMENTS

A preferred embodiment of the present invention is now described in detail in accordance with the accompanying drawings. However, the dimensions, materials, shapes and relative positions of the constituent parts shown in the embodiments should be changed as convenient depending on various conditions and on the structure of the apparatus adapted to the invention, and the invention is not limited to the embodiments described herein.

First Embodiment

Figure 1:
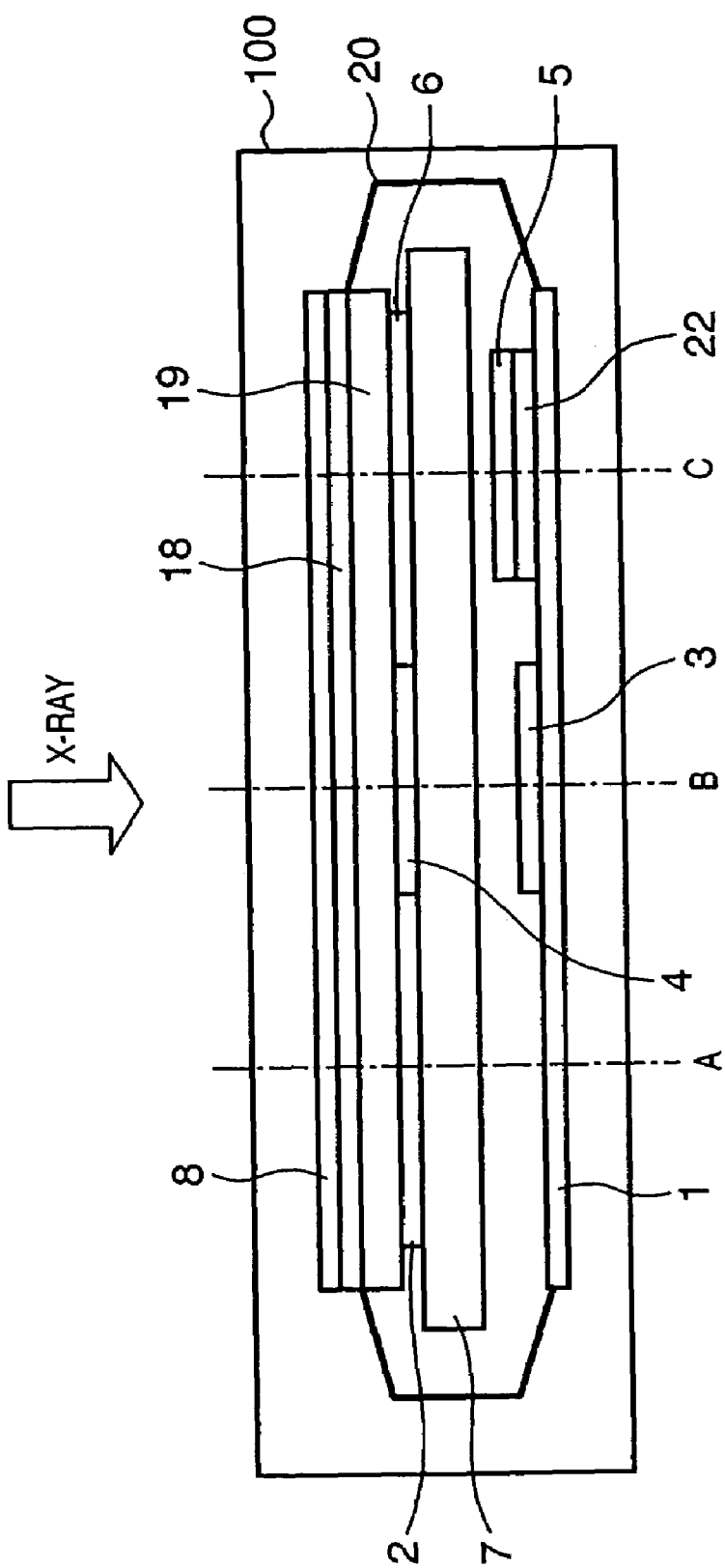
FIG. 1 is a diagram showing a schematic cross-sectional view of the structure of a radiographic apparatus according to a first embodiment of the present invention.
Figure 5:
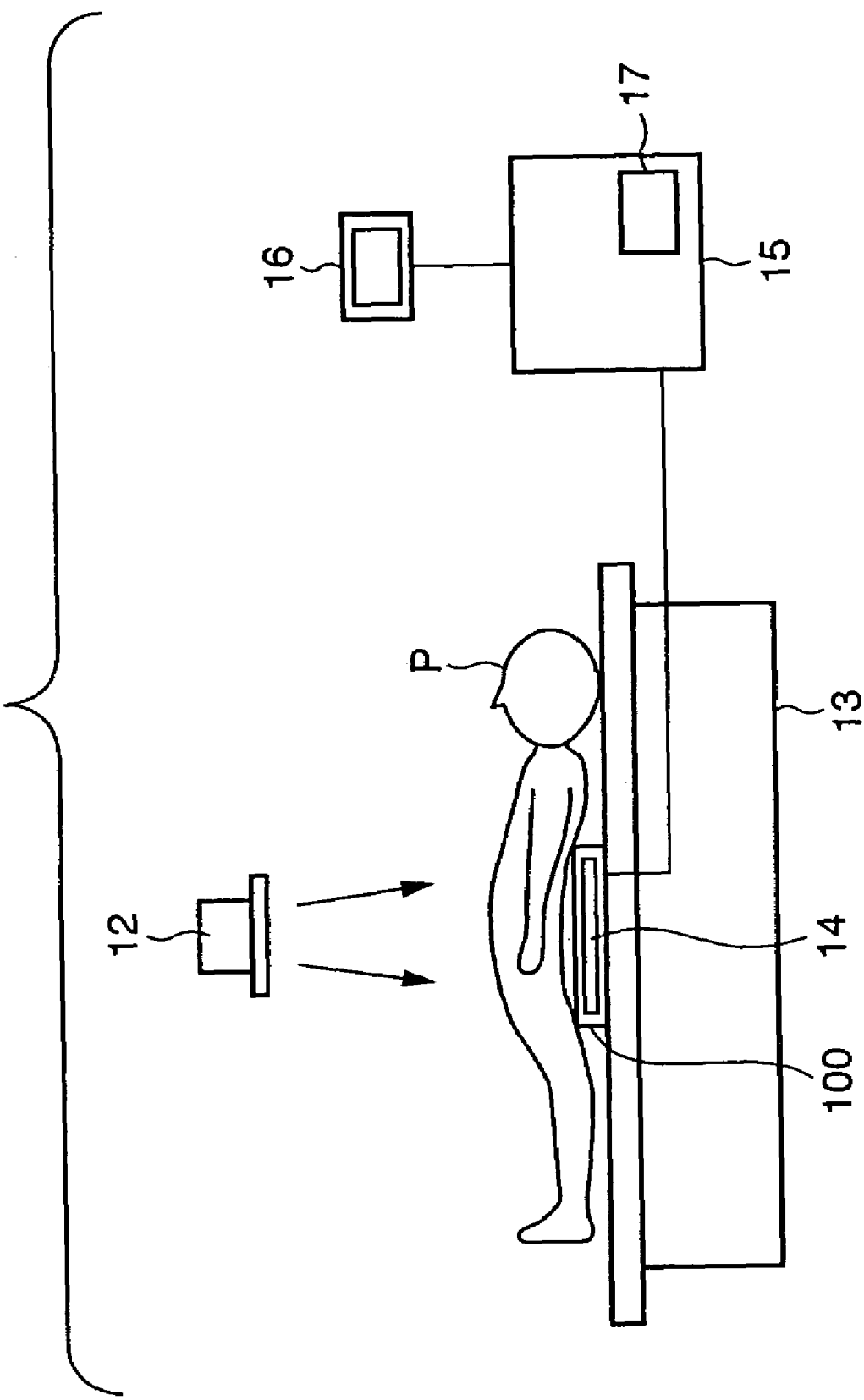
FIG. 5 is a schematic diagram of a photoelectric system that uses a conventional two-dimensional array sensor.

FIG. 1 is a diagram showing a schematic cross-sectional view of the structure of a radiographic apparatus according to a first embodiment of the present invention. It should be noted that constituent elements that are the same as those of the apparatus described in FIGS. 5–7 are given the same reference numbers, and a description thereof is omitted.

Figure 6:
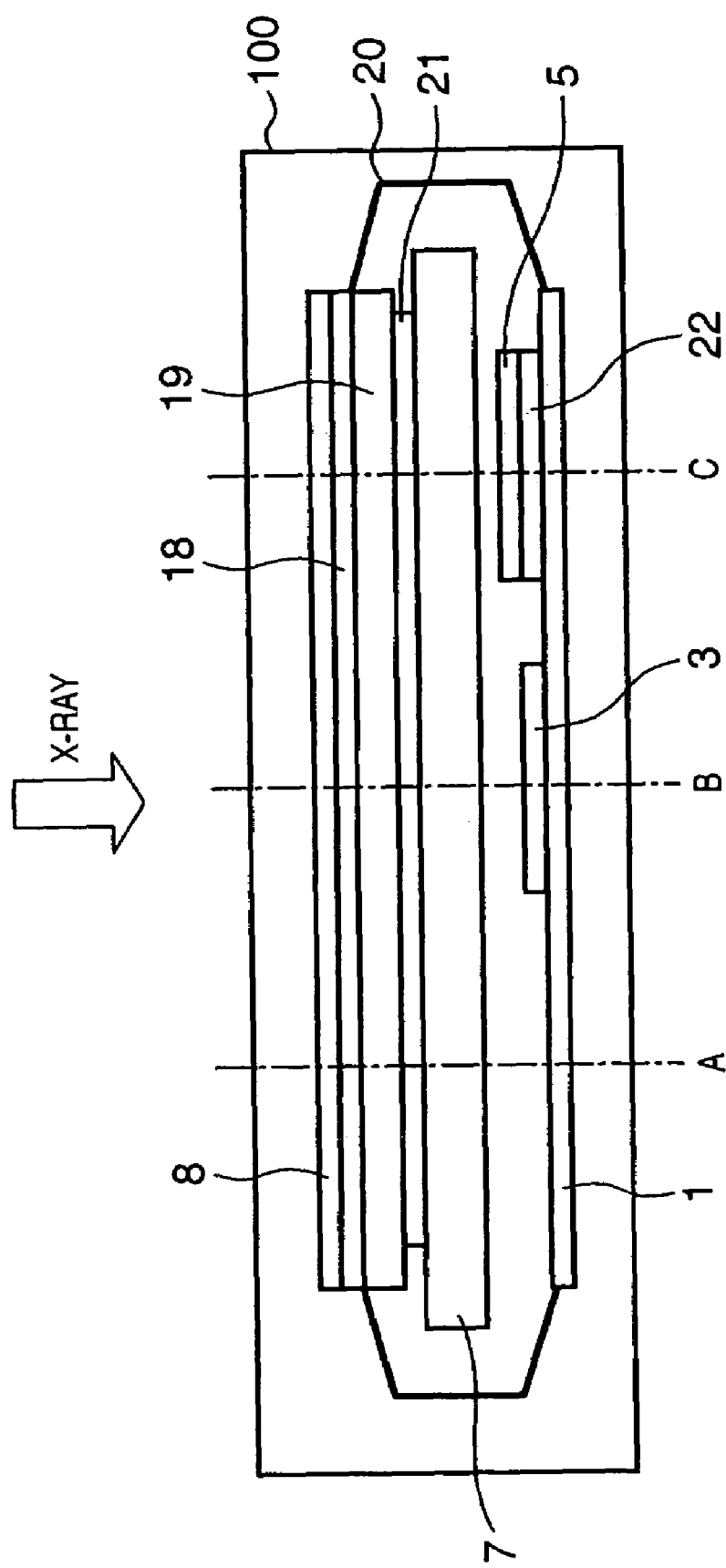
FIG. 6 is a diagram showing a schematic cross-sectional view of the internal arrangement of a conventional radiographic apparatus.

What is different from that shown in FIG. 6 is that an X-ray shield member using material that differs depending on the area is used instead of the X-ray shield member 21. In the example shown in FIG. 1, X-ray shield members 2, 4 and 6 are provided in areas disposed opposite the electrical circuit board 1, element 3 and protective layer 5, with the material of the X-ray shield members differing according to the positions of the elements. Materials are selected for the X-ray shield members 2, 4 and 6 so that the amount of scattered rays (the amount of backscattering) from the lower layer is approximately uniform.

Figure 2:
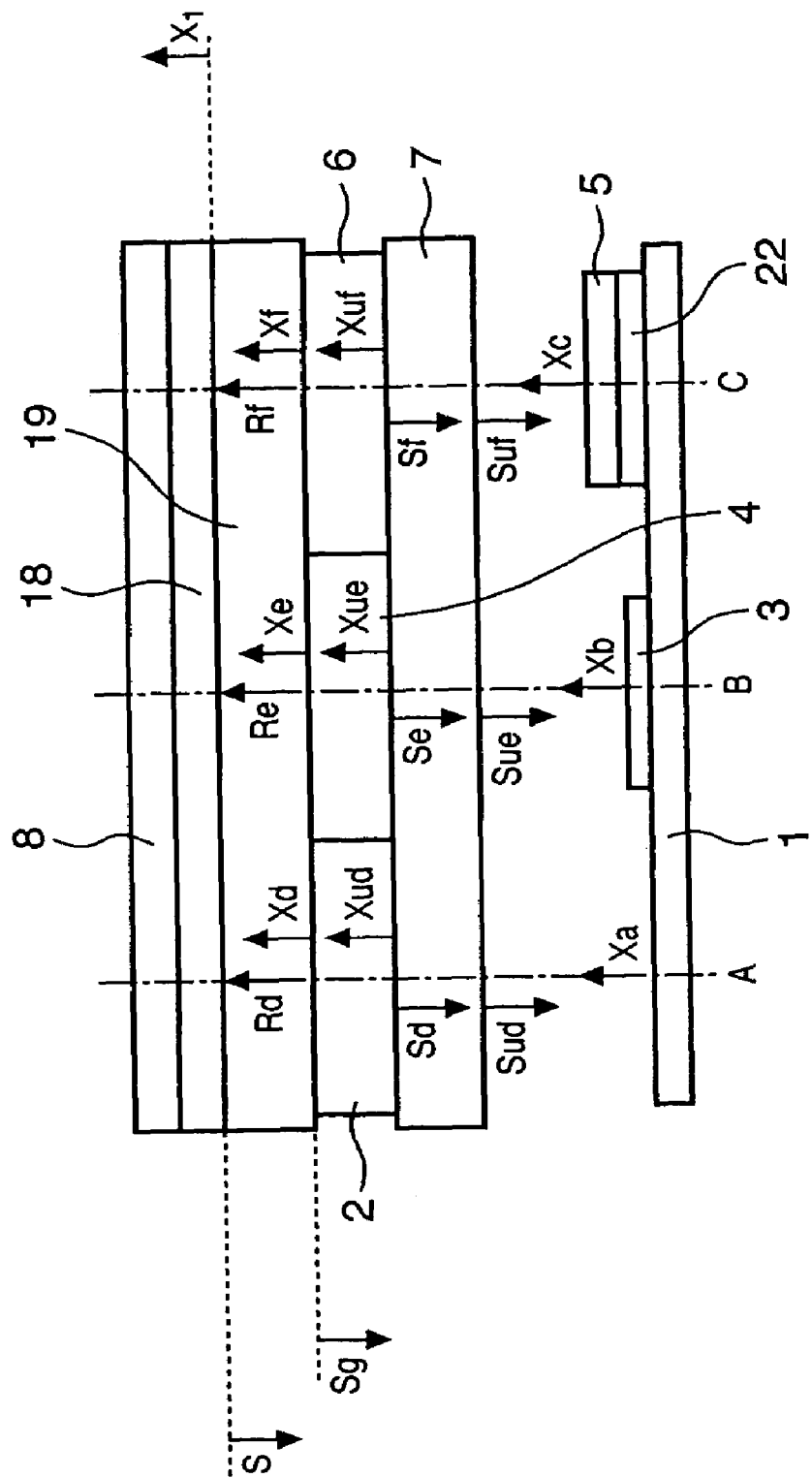
FIG. 2 is a diagram showing a schematic view of a state of X-ray radiation of the constituent elements of FIG. 1.

FIG. 2 is a diagram showing a schematic view of a state of X-ray radiation of the constituent elements of FIG. 1. For simplicity of description, the quality of the X-rays described below is monoenergetic. It should be noted that constituent parts that are the same as those described with respect to FIG. 1 are given the same reference numerals.

If the probability of scattering at the X-ray shield members 2, 4, 6 is Fs, Ms and Ws, respectively, then the amount of scattered rays per unit of surface area of the X-ray shield members 2, 4 and 6 Xd, Xe, Xf is $$Xd=Sg \cdot Fs$$
$$Xe=Sg \cdot Ms \qquad (9)$$
$$Xf=Sg \cdot Ws$$

Therefore, substituting the equation of (3) described above in the equations of (9) yields $$Xd=S \cdot Gt \cdot Fs$$
$$Xe=S \cdot Gt \cdot Ms \qquad (10)$$
$$Xf=S \cdot Gt \cdot Ws$$

Moreover, if the transmittivity of the X-ray shield member 2, 4 and 6 is Mt, Ft and Wt, respectively, then the amount of X-ray radiation passing through the X-ray shield members Sd, Se and Sf is $$Sd=Sg \cdot Ft$$
$$Se=Sg \cdot Mt \qquad (11)$$
$$Sf=Sg \cdot Wt$$

Therefore, substituting the equations of (3) described above in the equations of (11) yields $$Sd=S \cdot Gt \cdot Ft$$
$$Se=S \cdot Gt \cdot Mt \qquad (12)$$
$$Sf=S \cdot Gt \cdot Wt$$

Further, the amount of scattered rays Xud, Xue and Xuf from the base 7 at the areas A, B, and C where the X-ray shield members 2, 4 and 6 are disposed is $$Xud=Sd \cdot Us$$
$$Xue=Se \cdot Us \qquad (13)$$
$$Xuf=Sf \cdot Us$$

Therefore, substituting the equations of (12) described above in the equations of (13) yields $$Xud=S \cdot Gt \cdot Ft \cdot Us$$
$$Xue=S \cdot Gt \cdot Mt \cdot Us \qquad (14)$$
$$Xuf=S \cdot Gt \cdot Wt \cdot Us$$

Further, the amount of X-ray radiation Sud, Sue, and Suf, passing through the base 7 at the areas A, B, and C where the X-ray shield members 2, 4 and 6 are disposed is $$Xud=Sd \cdot Ut$$
$$Xue=Se \cdot Ut \qquad (15)$$
$$Xuf=Sf \cdot Ut$$

Therefore, substituting the equations of (12) described above in the equations of (15) yields $$Sud=S \cdot Gt \cdot Ft \cdot Ut$$
$$Sue=S \cdot Gt \cdot Mt \cdot Ut \qquad (16)$$
$$Suf=S \cdot Gt \cdot Wt \cdot Ut$$

Moreover, the amount of scattered rays Xa, Xb and Xc at the electrical circuit board 1, the element 3 and the protective layer 5, respectively, is $$Xa=Sud \cdot As$$
$$Xb=Sue \cdot Bs \qquad (17)$$
$$Xc=Suf \cdot Cs$$

Therefore, substituting the equations of (16) into the equations of (17) yields $$Xa=S \cdot Gt \cdot Ft \cdot Ut \cdot As$$
$$Xb=S \cdot Gt \cdot Mt \cdot Ut \cdot Bs \qquad (18)$$
$$Xc=S \cdot Gt \cdot Wt \cdot Ut \cdot Cs$$

The amount of X-ray radiation (backscattering) Rd, Re and Rf reaching the phosphor sheet 8 at each of the areas, respectively, is $$Rd=X1+Gt \cdot Xd+Gt \cdot Ft \cdot Xud+Gt \cdot Ft \cdot Ut \cdot Xa$$
$$Re=X1+Gt \cdot Xe+Gt \cdot Ft \cdot Xue+Gt \cdot Ft \cdot Ut \cdot Xb \qquad (19)$$
$$Rf=X1+Gt \cdot Xf+Gt \cdot Ft \cdot Xuf+Gt \cdot Ft \cdot Ut \cdot Xc$$

Therefore, substituting the equations of (1), (10), (14) and (18) in the equations of (19) yields $$Rd=S \cdot Gs+S \cdot Gt^2 \cdot Fs+S \cdot Gt^2 \cdot Ft^2 \cdot Us+S \cdot Gt^2 \cdot Ft^2 \cdot Ut^2 \cdot As$$
$$Re=S \cdot Gs+S \cdot Gt^2 \cdot Ms+S \cdot Gt^2 \cdot Mt^2 \cdot Us+S \cdot Gt^2 \cdot Mt^2 \cdot Ut^2 \cdot Bs \qquad (20)$$
$$Rf=S \cdot Gs+S \cdot Gt^2 \cdot Ws+S \cdot Gt^2 \cdot Wt^2 \cdot Us+S \cdot Gt^2 \cdot Wt^2 \cdot Ut^2 \cdot Cs$$

In order to reduce the difference in contrast due to backscattering at the radiographic image acquired by two-dimensional array sensor 14, it is desirable that the values for Rd, Re and Rf be substantially equal. Therefore, the materials for each of the X-ray shield members 2, 4 and 6 may be selected so that Rd, Re and Rf are approximately equal with the scattering probability Fs, Ms and Ws and the transmittivity Ft, Mt and Wt at the X-ray shield members 2, 4 and 6, respectively, being variables. By so doing, it is possible to obtain a shield member that includes a plurality of areas in which at least one of the radiation transmittivity and the radiation scattering probability is different. Here, at least one of the radiation transmittivity and the radiation scattering probability of the plurality of areas is selected so that the amount of scattered rays passing through the plurality of areas and projected into an imager is approximately uniform. It should be noted that the imager is the constituent elements that convert the radiation into image signals, and in the present embodiment is configured so as to include the phosphor sheet 8 and the photoelectric converter elements 18.

As material for the X-ray shield member, for example, there is molybdenum (Mo), tungsten (W) and iron (Fe). With uniform rays, X-ray transmittivity increases in order from W to Mo to Fe. Assuming, hypothetically, that the probability of scattering by the constituent elements of the lower layer decreases in order from the protective layer 5 to the element 3 to the electrical circuit board 1, then in order to minimize the difference in scattering amount at each area it is preferable, for example, to select Fe for the X-ray shield member 2, Mo for the X-ray shield member 4 and W for the X-ray shield member 6. However, because the material utilized for the X-ray shield members depends on the amount of scattered rays from the lower layer, it is preferable to select the material according to the structure of the lower levels, and the material is not limited to the three types described above.

By providing X-ray shield members of different materials depending on the amount of scattered rays at each area, it is possible to use an X-ray shield member having a relatively high X-ray transmittivity in areas for which the amount of scattered rays is small. Since a high X-ray transmittivity means a relatively low density of material, such an arrangement makes it possible to hold down the weight of the apparatus. Moreover, if the amount of scattered rays at a given area is so small that it does not affect the clarity of the image, then it is also possible to not provide any X-ray shield member at such area. In addition, in the first embodiment of the present invention, although the material of the X-ray shield member is changed depending on the structure on the electrical circuit board 1, alternatively, for example, the material for the X-ray shield member can also be selected depending on the structure or shape of the base, etc., or the disposition of other constituent elements. In other words, when the amount of backscatter on the phosphor sheet differs by location due to electronic components or the mechanical structure and the like, the invention according to the present embodiment can be adapted thereto.

As described above, according to the first embodiment of the present invention, by replacing the X-ray shield member made of a uniform material and disposed opposite practically the entire image detection effective area surface of the conventional radiation image sensor with a plurality of members whose material differs depending on the constituent elements of the lower layer, the effect of scattered rays from the lower layer can be restrained while achieving a relative reduction in the weight of the apparatus. With an electronic cassette in particular, weight reduction greatly influences operability and is very effective. Moreover, because molybdenum (Mo), tungsten (W) and iron (Fe), which are easier to install, can be used for the X-ray shield member, thus making more effective installation possible.

Second Embodiment

Figure 3:
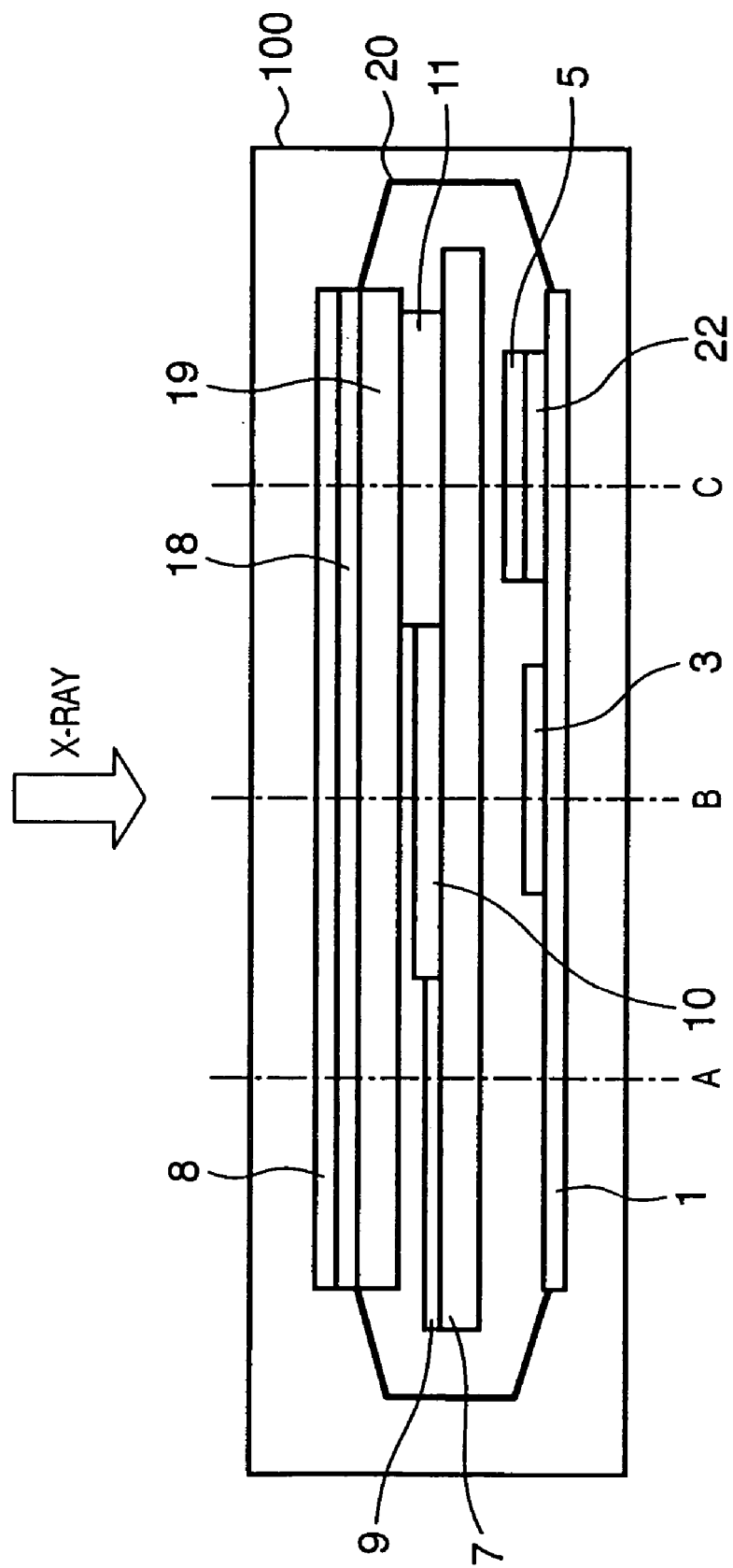
FIG. 3 is a diagram showing a schematic cross-sectional view of the structure of a radiographic apparatus according to a second embodiment of the present invention.

FIG. 3 is a diagram showing a schematic cross-sectional view of the structure of a radiographic apparatus according to a second embodiment of the present invention. It should be noted that constituent elements identical to those described in FIG. 1 are given the same reference numerals, and a description thereof is omitted.

What is different from FIG. 1 is that the X-ray shield member has different thicknesses depending on the area. Specifically, a thin X-ray shield member 9 is provided for an area A disposed opposite the electrical circuit board 1, a intermediate X-ray shield member 10 is provided for an area B disposed opposite the element 3, and a thick X-ray shield member 11 is provided for an area C disposed opposite the protective layer 5, thus changing the thickness of the X-ray shield members depending on the disposition of the elements. The thickness of each of the X-ray shield members 9, 10 and 11 is varied so that the amount of scattered rays from the lower layer is approximately uniform.

Figure 4:
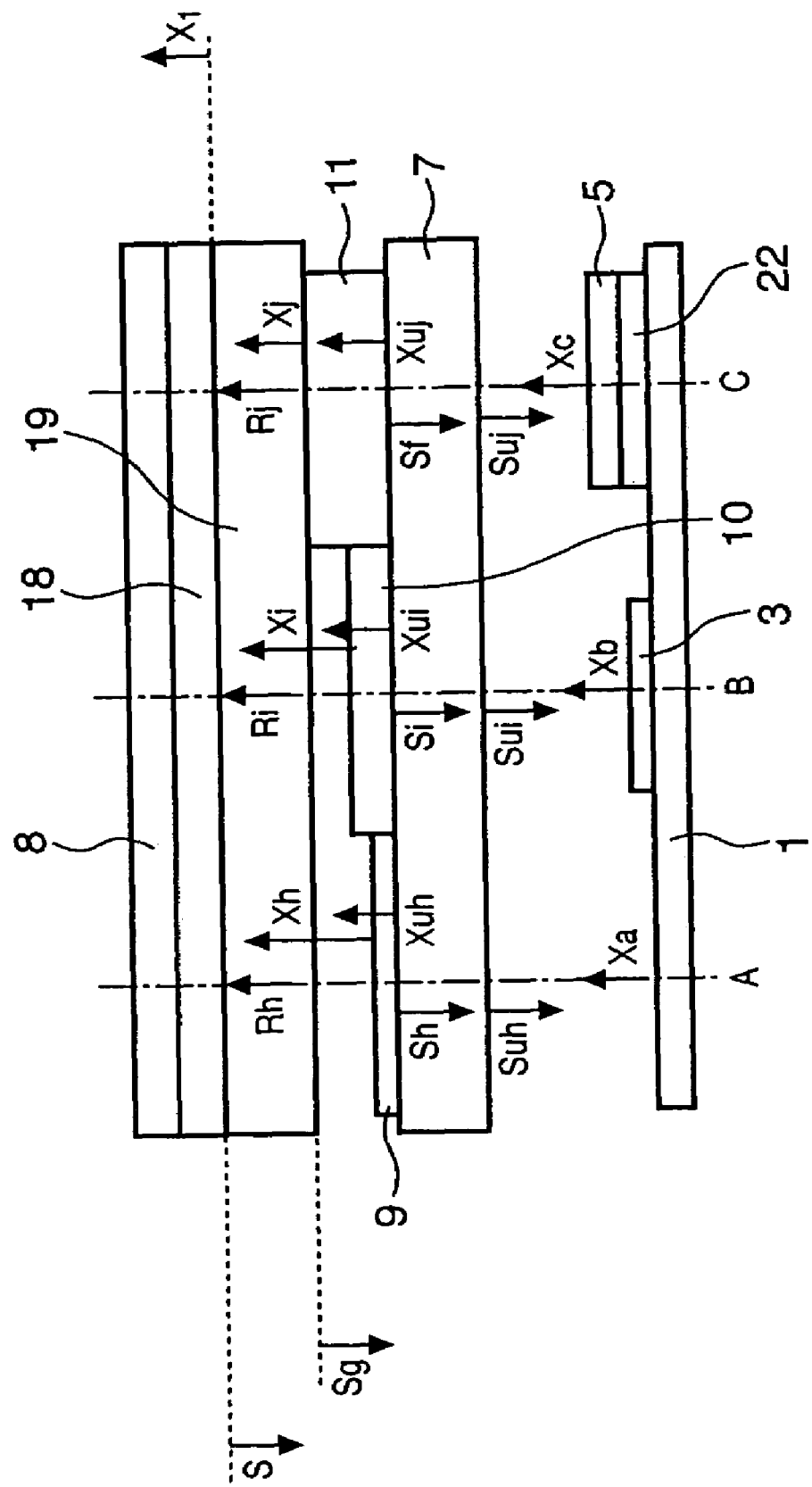
FIG. 4 is a diagram showing a schematic view of a state of X-ray radiation of the constituent elements of FIG. 3.

FIG. 4 is an illustrating diagram for the purpose of estimating in a general way the amount of backscattering that occurs at the areas disposed opposite the elements in FIG. 3. For simplicity, the quality of the X-rays are assumed to be monoenergetic. It should be noted that constituent elements identical to those described in FIG. 3 described above are given the same reference numerals.

The equations correlating the amount of scattered rays returning to the phosphor sheet 8 with the scattering probability and transmittivity of the X-ray shield members 9, 10 and 11 of different thicknesses are the same as the equations for the X-ray shield members 2, 4 and 6 of different materials as described above.

Therefore, if the probability of scattering for the X-ray shield members 9, 10 and 11 of different thicknesses is $\alpha s$, $\beta s$ and $\gamma s$, respectively, and the scattering amount per unit of surface area of the X-ray shield members 9, 10 and 11 is Xh, Xi and Xj, respectively, and the transmittivity of the X-ray shield members 9, 10 and 11 is $\alpha t$, $\beta t$ and $\gamma t$, respectively, with the amount of scattered rays from the base 7 in areas A, B and C corresponding to the positions at which the X-ray shield members 9, 10 and 11 are provided being Xuh, Xui and Xuj, respectively, and the amount of radiation passing through the base 7 in the areas A, B and C being Suh, Sui and Suj, respectively, then the amount of scattered rays Xa, Xb and Xc at the electrical circuit board 1, the element 3 and the protective layer 5, respectively, replacing the Sud, Sue and Suf of equation (17) with Suh, Sui and Suj, respectively, becomes $$Xa = Suh \cdot As$$

$$Xb = Sui \cdot Bs \quad (21)$$

$$Xc = Suj \cdot Cs$$

Therefore, $$Xa = S \cdot Gt \cdot \alpha t \cdot Ut \cdot As$$

$$Xb = S \cdot Gt \cdot \beta t \cdot Ut \cdot Bs \quad (22)$$

$$Xc = S \cdot Gt \cdot \gamma t \cdot Ut \cdot Cs$$

The amount of scattered rays Rh, Ri and Rj returning to the phosphor sheet 8 is $$Rh = X1 + Gt \cdot Xh + Gt \cdot \alpha t \cdot Xuh + Gt \cdot \alpha t \cdot Ut \cdot Xa$$

$$Ri = X1 + Gt \cdot Xi + Gt \cdot \beta t \cdot Xui + Gt \cdot \beta t \cdot Ut \cdot Xb \quad (23)$$

$$Rj = X1 + Gt \cdot Xj + Gt \cdot \gamma t \cdot Xuj + Gt \cdot \gamma t \cdot Ut \cdot Xc$$

Therefore, $$Rh = S \cdot Gs + S \cdot Gt^2 \cdot \alpha s + S \cdot Gt^2 \cdot \alpha t^2 \cdot Us + S \cdot Gt^2 \cdot \alpha t^2 \cdot Ut^2 \cdot As$$

$$Ri = S \cdot Gs + S \cdot Gt^2 \cdot \beta s + S \cdot Gt^2 \cdot \beta t^2 \cdot Us + S \cdot Gt^2 \cdot \beta t^2 \cdot Ut^2 \cdot Bs \quad (24)$$

$$Rj = S \cdot Gs + S \cdot Gt^2 \cdot \gamma s + S \cdot Gt^2 \cdot \gamma t^2 \cdot Us + S \cdot Gt^2 \cdot \gamma t^2 \cdot Ut^2 \cdot Cs$$

As with the first embodiment described above, in order to reduce the difference in contrast due to backscattering at the radiographic image acquired by two-dimensional array sensor 14, it is desirable that the values for Rh, Ri and Rj be substantially equal. Therefore, the materials for each of the X-ray shield members 9, 10 and 11 may be selected so that Rh, Ri and Rj are approximately equal with the probability of scattering $\alpha s$, $\beta s$ and $\gamma s$ and the transmittivity $\alpha t$, $\beta t$ and $\gamma t$ at the X-ray shield members 9, 10 and 11, respectively, being variables. By so doing, it is possible to obtain a shield member that includes a plurality of areas in which at least one of the radiation transmittivity and the radiation scattering probability is different. Here, at least one of the radiation transmittivity or the radiation scattering probability of the plurality of areas is selected so that the amount of scattered rays passing through the plurality of areas and projected into an imager is approximately uniform. It should be noted that the imager is the constituent elements that convert the radiation into image signals, and in the present embodiment is configured so as to include the phosphor sheet 8 and the photoelectric converter elements 18.

The X-ray transmittivity of uniform rays increases as the thickness of the shield member decreases, from thick to intermediate to thin when the quality of the X-rays is monoenegetic. Assuming, hypothetically, that the probability of scattering by the constituent elements of the lower layer decreases in order from the protective layer 5 to the element 3 to the electrical circuit board 1, then in order to minimize the difference in scattering amount at each area it is preferable to make the X-ray shield member 9 thin, give the X-ray shield member 10 an intermediate thickness and make the X-ray shield member 11 thick. FIGS. 3 and 4 show a structure based on this assumption. Moreover, as material for the X-ray shield member, as described above, the use of molybdenum (Mo), tungsten (W) and iron (Fe) instead of lead (Pb) eases handling and installation. However, the thickness of the X-ray shield members, because it depends on the amount of scattered rays from the lower layer and on the material of the X-ray shield members, is selected in accordance therewith.

By providing an X-ray shield member whose thickness varies with each area as described above, it is possible to use a relatively thin X-ray shield member in areas in which the amount of scattered rays is small, and therefore the overall weight of the X-ray shield member can be held down. Moreover, if the amount of scattered rays at a given area is so small that it does not affect the clarity of the image, then it is also possible to not provide any X-ray shield member at such area. Further, if combined with the use of X-ray shield members composed of different materials as described in the first embodiment, means capable of reducing the difference in contrast are further increased and therefore such combination is very effective. In the second embodiment of the present invention, although the thickness of the X-ray shield member is changed depending on the structure on the electrical circuit board 1, alternatively, for example, the thickness of the X-ray shield member can also be selected depending on the structure or shape of the base, etc., or the disposition of other constituent elements. In other words, when the amount of backscatter on the phosphor sheet differs by location due to the electronic components or the mechanical structure and the like, the invention according to the present embodiment can be adapted thereto.

As described above, according to the second embodiment of the present invention, by replacing the X-ray shield member made of a uniform material and disposed opposite practically the entire image detection effective area surface of the conventional radiation image sensor with a plurality of members whose thickness differs depending on the constituent elements of the lower layer, the effect of scattered rays from the lower layer can be restrained while achieving a relative reduction in the weight of the apparatus. With an electronic cassette in particular, weight reduction greatly influences operability and is very effective.

The present invention is not limited to the above embodiments, and various changes and modifications can be made within the spirit and scope of the present invention. Therefore, to apprise the public of the scope of the present invention, the following claims are made.

What is claimed is:

1. A radiographic apparatus comprising:
    an imaging unit for converting a radiation image of an object into an image signal; and
    a shield member for shielding said imaging unit from scattered rays arising inside the radiographic apparatus from radiation passing through said imaging unit, said shield member including a plurality of areas in which either a radiation transmittivity or a radiation scattering probability, or both, differs;
    wherein either the radiation transmittivity or the radiation scattering probability, or both, of the plurality of areas is selected so that an amount of scattered rays passing through the plurality of areas and entering said imaging unit is uniform, and
    wherein the plurality of areas are composed of different materials.

2. The recording apparatus according to claim 1, wherein the material includes at least one of molybdenum (Mo), tungsten (W) and iron (Fe).

3. The radiographic apparatus according to claim 1, wherein a thickness of the plurality of areas differs.

4. The radiographic apparatus according to claim 1, wherein constituent elements causing the scattered rays include either an electronic component or a mechanical structure, or both.

5. The radiographic apparatus according to claim 1, wherein the radiographic apparatus is of cassette-type.

* * * * *